(12) United States Patent
Meng et al.

(10) Patent No.: US 9,867,644 B2
(45) Date of Patent: Jan. 16, 2018

(54) BONE IMPLANT (71) Applicants: Sheng-Hui Meng, Kaohsiung (TW); Shao-Bu Hu, Kaohsiung (TW)

(72) Inventors: Sheng-Hui Meng, Kaohsiung (TW); Shao-Bu Hu, Kaohsiung (TW)

( * ) Notice: Subject to any disclaimer, the term of this patent is extended or adjusted under 35 U.S.C. 154(b) by 340 days.

(21) Appl. No.: 14/764,611

(22) PCT Filed: May 20, 2013

(86) PCT No.: PCT/CN2013/075937
§ 371 (c)(1),
(2) Date: Jul. 30, 2015

(87) PCT Pub. No.: WO2014/117456
PCT Pub. Date: Aug. 7, 2014

(65) Prior Publication Data
US 2015/0366599 A1 Dec. 24, 2015

(30) Foreign Application Priority Data

Feb. 1, 2013 (CN) .......................... 2013 1 0058537

(51) Int. Cl.
*A61B 17/04* (2006.01)
*A61B 17/86* (2006.01)
(Continued)

(52) U.S. Cl.
CPC ............ *A61B 17/863* (2013.01); *A61B 17/86* (2013.01); *A61C 8/00* (2013.01); *A61C 8/0018* (2013.01); *A61C 8/0025* (2013.01); *A61C 8/0045* (2013.01)

(58) Field of Classification Search
None
See application file for complete search history.

(56) References Cited

U.S. PATENT DOCUMENTS 5,425,407 A * 6/1995 Archuleta ............... B29C 73/06
152/370
8,118,849 B2 2/2012 Wahl et al.
(Continued)

FOREIGN PATENT DOCUMENTS

CN 201197743 Y 2/2009
CN 201384559 Y 1/2010
(Continued)

*Primary Examiner* — Sameh Boles
(74) *Attorney, Agent, or Firm* — Alan D. Kamrath; Kamrath IP Lawfirm, P.A.

(57) ABSTRACT

A bone implant includes: a body including a connection end and a drill end respectively on two ends thereof, with the body including a plurality of engagement sections between the connection end and the drill end, with a disengagement prevention section provided between two adjacent engagement sections, with each engagement section including a drilling thread disposed on an outer periphery of the body, with the drilling threads of the engagement sections having the same thread direction, with the disengagement prevention section including a coupling section on the outer periphery of the body, and with the disengagement prevention section having a maximum outer diameter smaller than a minimum outer diameter of each engagement section between the disengagement prevention section and the connection end; and an abutment seat mounted on the connection end of the body, with the abutment seat including a keying recess.

18 Claims, 7 Drawing Sheets

(51) Int. Cl.
*A61F 2/08* (2006.01)
*A61C 8/00* (2006.01)

(56) References Cited

U.S. PATENT DOCUMENTS

| | | |
|---|---|---|
| 2010/0216093 A1 | 8/2010 | Krush et al. |
| 2011/0276095 A1 | 11/2011 | Bar et al. |
| 2012/0225408 A1 | 9/2012 | Moore |

FOREIGN PATENT DOCUMENTS

| | | |
|---|---|---|
| CN | 201492492 U | 6/2010 |
| CN | 102300508 A | 12/2011 |
| WO | WO9109572 A1 | 7/1991 |
| WO | WO2011053170 A | 5/2011 |

* cited by examiner

BONE IMPLANT

BACKGROUND OF THE INVENTION

1. Field of the Invention

The present invention relates to a bone implant and, more particularly, to a bone implant that includes threads and that will not be removed after implantation into a bone.

2. Description of the Related Art

There is a wide variety of bone implants. Bone needles, bone nails, bone screws for locking implants, such as bone plates or artificial joints, intramedullary nails, or dental implants are common bone implants. Generally, the engagement stability between every type of bone implant and the bone is critical. A bone implant securely engaged with the bone can increase the medical effect and efficiency to be achieved.

Most of the bone implants are not removed after implantation into the bones. Taking a dental implant as an example, Taiwan Patent Publication No. 201121510 entitled "HUMAN BODY IMPLANT AND MANUFACTURING METHOD THEREFOR" focuses on improvement on the material of the surface of the dental implant. Taiwan Publication No. M338055 entitled "IMPROVED DENTAL IMPLANT STRUCTURE" focuses on the engagement reliability between the neck of the dental implant and the bone. Taiwan Publication No. M390130 entitled "ONE-PIECE ANGLE DENTAL IMPLANT" focuses on improvement on the abutment of the dental implant.

However, none of the above dental implants provides a thread with a structure capable of preventing sliding/disengagement movement in the reverse direction, such that the tooth implant that has implanted into an alveolar bone can only securely engage with the alveolar bone after the osseointegration between the bone tissues and the dental implant. In a case that the dental implant is subject to a force opposite to the thread direction during the osseointegration, the dental implant could have rotational movement and, thus, results in disengagement. Even the displacement is slight, the bone tissues could be loosened from the surface of the dental implant, leading to failure in the osseointegration. In view of the above reasons, improvement to the current bone implants is desired.

SUMMARY OF THE INVENTION

An objective of the present invention is to provide a bone implant which can provide a resistance opposite to the disengagement direction of the bone implant to effectively avoid the bone implant from becoming loosened in the bone, such that the bone implant can reliably engage in the bone without the risks of disengagement due to sliding in the reverse direction.

To achieve the above objective, the technical content utilized by the present invention includes a bone implant including: a body including a connection end and a drill end respectively on two ends thereof, with the body including a plurality of engagement sections between the connection end and the drill end, with a disengagement prevention section provided between two adjacent engagement sections, with each of the plurality of engagement sections including a drilling thread disposed on an outer periphery of the body, with the drilling threads of the plurality of engagement sections having the same thread direction, with the disengagement prevention section including a coupling section on the outer periphery of the body, and with the disengagement prevention section having a maximum outer diameter smaller than a minimum outer diameter of each of the plurality of engagement sections between the disengagement prevention section and the connection end; and an abutment seat mounted on the connection end of the body, with the abutment seat including a keying recess.

The present invention further provides a bone implant including: a body including a connection end and a drill end respectively on two ends thereof, with the body including a plurality of engagement sections between the connection end and the drill end, with a disengagement prevention section provided between two adjacent engagement sections, with each of the plurality of engagement sections including a drilling thread disposed on an outer periphery of the body, with the drilling threads of the plurality of engagement sections having the same thread direction, with the disengagement prevention section including a coupling section on the outer periphery of the body, and with the disengagement prevention section having a maximum outer diameter smaller than a minimum outer diameter of each of the plurality of engagement sections between the disengagement prevention section and the connection end; and a restraining head mounted on the connection end of the body.

In the bone implant according to the present invention, the coupling section is at least one disengagement prevention thread disposed on the outer periphery of the body, and the disengagement prevention thread has a thread direction different from the thread direction of the drilling threads.

In the bone implant according to the present invention, the number of the disengagement prevention thread is plural.

In the bone implant according to the present invention, a separation portion is provided between two adjacent disengagement prevention threads, and the separation portion is a blank section free of threads or having a protrusion.

In the bone implant according to the present invention, the coupling section is at least one protruding ring disposed on the outer periphery of the body.

In the bone implant according to the present invention, the number of the protruding ring is plural.

In the bone implant according to the present invention, a separation portion is provided between two adjacent disengagement prevention threads, and the separation portion is a blank section free of threads or having a protrusion.

In the bone implant according to the present invention, the coupling section is a rugged face.

In the bone implant according to the present invention, the coupling section is at least one helical groove or annular groove disposed on the outer periphery of the body.

In the bone implant according to the present invention, the plurality of drilling threads has an identical thread angle.

| Reference Numbers of Main Elements | |
|---|---|
| 1 body | 1a connection end |
| 1b drill end | 11 engagement section |
| 111 drilling thread | 112 groove section |
| 12 disengagement prevention section | 121 coupling section |
| 121a disengagement prevention thread | 121b protruding ring |
| 121c helical groove | 122 separation portion |
| 2 abutment seat | 21 keying recess |
| 3 body | 3a connection end |
| 3b drill end | 31 engagement section |
| 311 drilling thread | 312 groove portion |
| 32 disengagement prevention section | 321 coupling section |
| 321a disengagement prevention thread | |
| 4 restraining head | 41 tool abutting portion |
| 5 bone plate | 51 drill hole |
| D1 minimum outer diameter | D2 maximum outer diameter |
| D3 minimum outer diameter | D4 maximum outer diameter |
| A abutment | |

DETAILED DESCRIPTION OF THE INVENTION

The above and other purposes, features and advantages of the present invention will become clearer in light of the following detailed description of preferred embodiments of this invention described in connection with the drawings.

Figure 1:
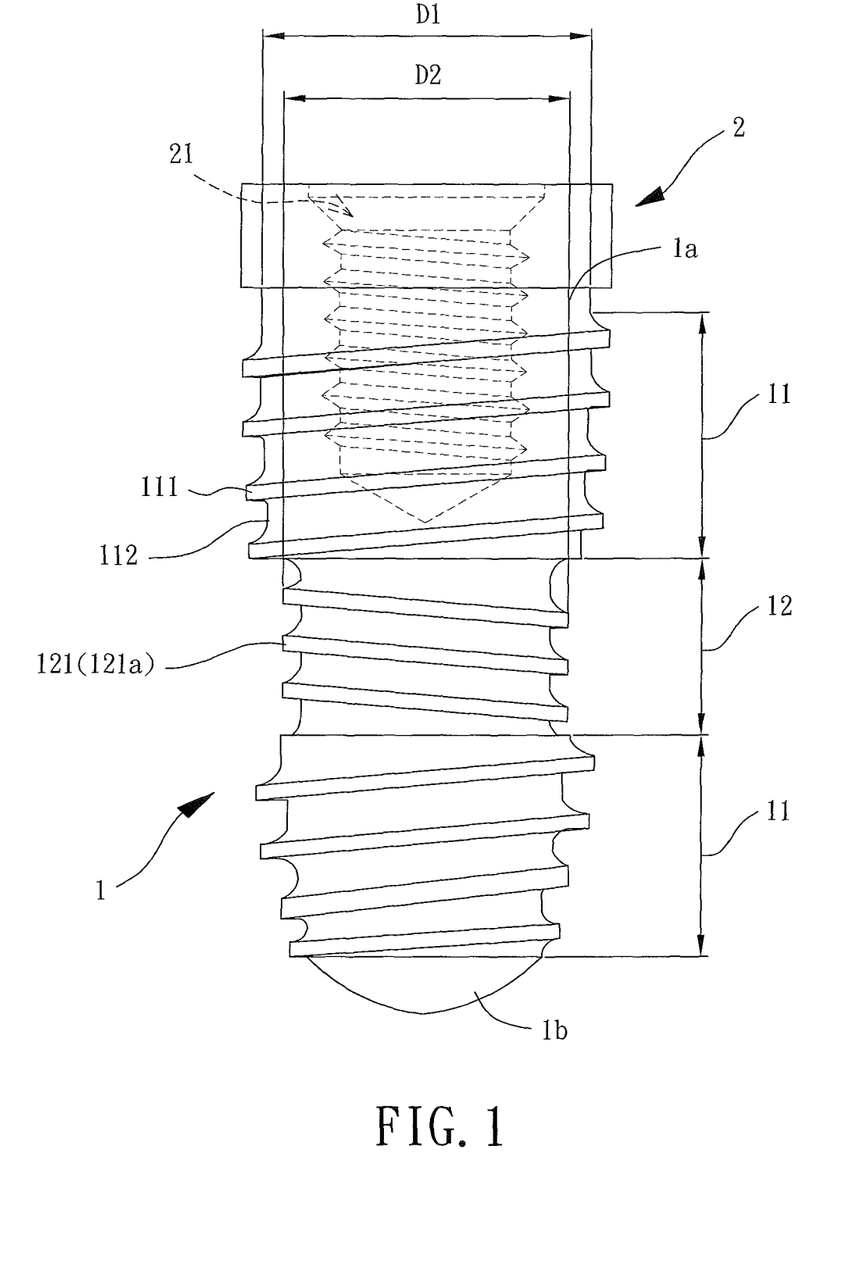
FIG. 1 is a first diagrammatic view of a structure of a first embodiment according to the present invention.

With reference to FIG. 1, a bone implant of the first embodiment according to the present invention is a dental implant. The dental implant includes a body 1 and an abutment seat 2. The abutment seat 2 is mounted on an end of the body 1.

The body 1 includes a connection end 1a and a drill end 1b respectively on two ends thereof. The connection end 1a of the body 1 is connected to the abutment seat 2. The drill end 1b is preferably arcuate or pointed. In an exemplified example shown in the illustrative drawings of this embodiment, the drill end 1b is arcuate. The body 1 includes a plurality of engagement sections 11 between the connection end 1a and the drill end 1b. A disengagement prevention section 12 is provided between two adjacent engagement sections 11. In the exemplified example shown in the illustrative drawings of this embodiment, the body 1 includes two engagement sections 11 and a disengagement prevention section 12.

In this embodiment, each engagement section 11 includes a drilling thread 111 disposed on an outer periphery of the body 1. The drilling threads 111 of the engagement sections 11 have the same thread direction and preferably have the same thread angle. A groove section 112 is formed in the pitch of each drilling thread 111. The body 1 includes a minimum outer diameter D1 at the groove section 112 of each engagement section 11. The disengagement prevention section 12 includes a coupling section 121 on the outer periphery of the body 1. The body 1 includes a maximum outer diameter D2 at the disengagement prevention section 12. To prevent the smoothness from being affected while locking each engagement section 11 into a bone, the maximum outer diameter D2 should be smaller than the minimum outer diameter D1 of each engagement section 11 between the disengagement prevention section 12 and the connection end 1a.

In this embodiment, the coupling section 121 can be at least one disengagement prevention thread 121a disposed on the outer periphery of the body 1. Thus, the disengagement prevention section 12 can be in the form of a neck, such that the maximum outer diameter D2 of the disengagement prevention section 12 can be smaller than the minimum outer diameter D1 of the engagement section 11 between the disengagement prevention section 12 and the connection end 1a. Thus, when each engagement section 11 of the body 1 of the dental implant is drilling and locking into the bone, the disengagement prevention section 12 will not affect the smoothness of the locking. The disengagement prevention thread 121a has a thread direction different from the thread direction of the drilling threads 111 to provide a torque opposite to the drilling threads 111.

Figure 2:
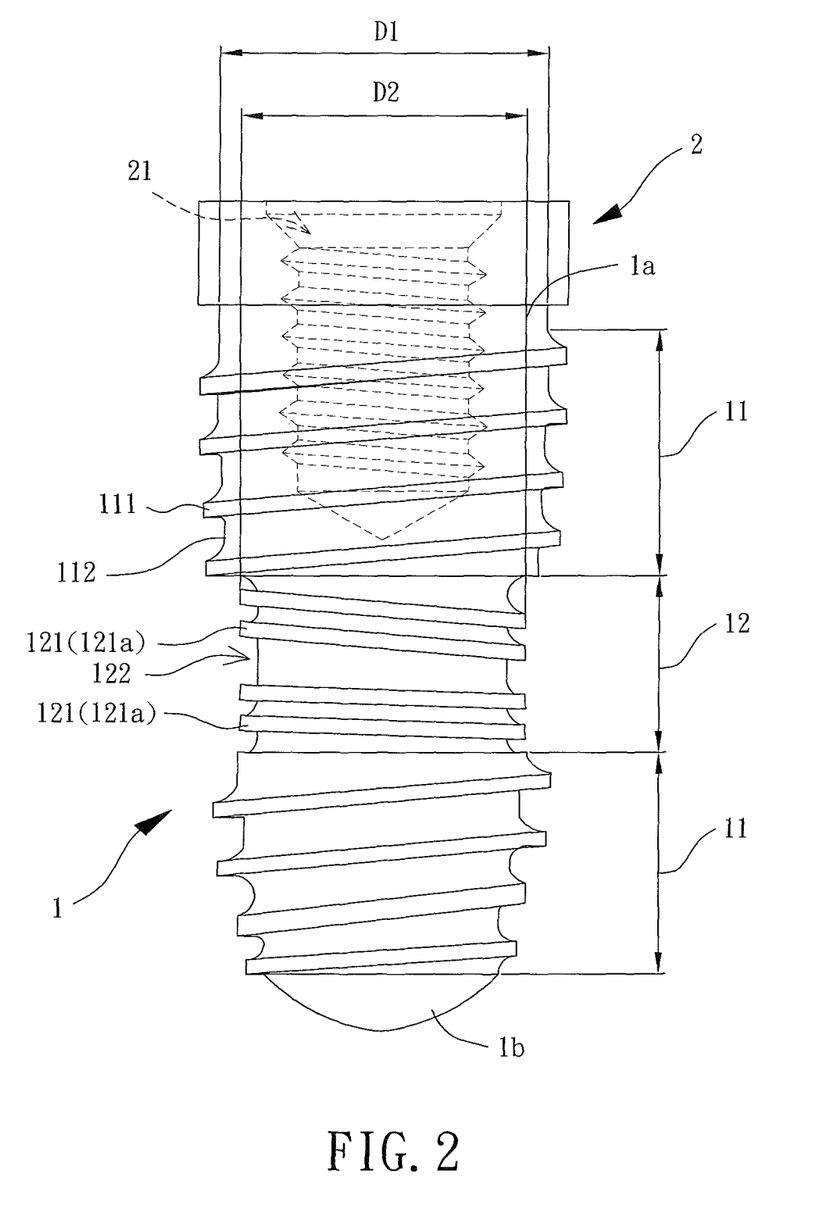
FIG. 2 is a second diagrammatic view of the structure of the first embodiment according to the present invention.

With further reference to FIG. 2, in a case that the disengagement prevention section 12 includes a plurality of disengagement prevention threads 121a, the pitches, the thread angles, and the depths of the disengagement prevention threads 121a can be different. Alternatively, a separation portion 122 can be provided between two adjacent disengagement prevention threads 121a. The separation portion 122 can be a blank section free of threads to present a smooth or rugged face. Alternatively, the separation portion 122 can have annular patterns or a protrusion in any form. The present invention is not limited in this regard.

The abutment seat 2 can be integrally connected to the connection end 1a of the body 1. The abutment seat 2 includes a keying recess 21 therein for coupling and positioning an abutment A (see FIG. 3). The abutment A is connected to a crown (not shown) to form an artificial tooth. However, the structure of the abutment seat can be modified in response to abutments of different forms, which can be appreciated by a person having ordinary skill in the art and which is not the features of the invention and is, therefore, not redundantly described hereinafter, nor should it be restricted to the illustrated forms.

Figure 3:
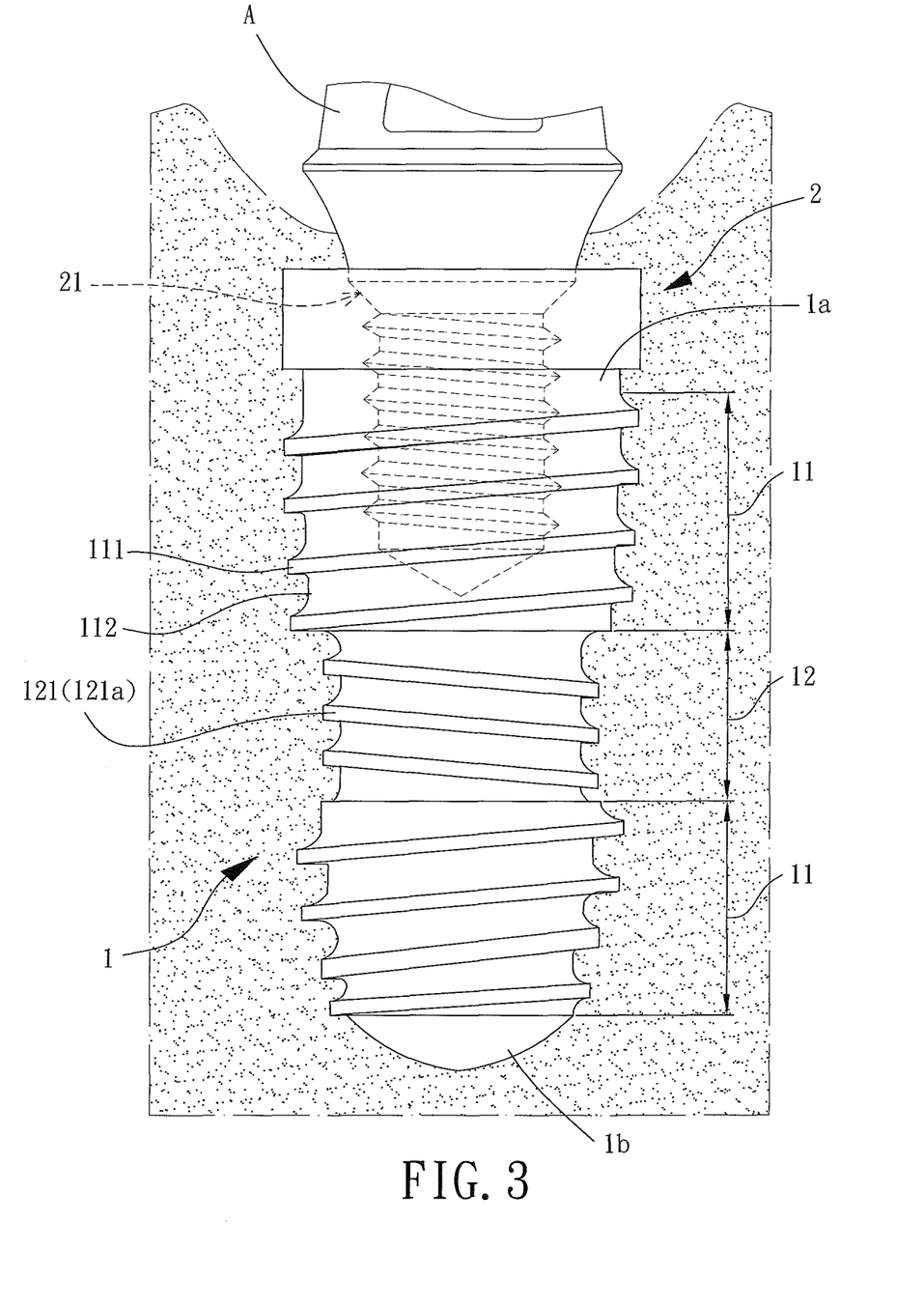
FIG. 3 is a diagrammatic view illustrating practice of the first embodiment according to the present invention.

With reference to FIG. 3, during a dental therapy, a hole (not shown) is generally drilled in the gum and the alveolar bone in advance. Then, the drill end 1b of the dental implant is used as an implantation end, and the body 1 is rotated in the thread direction of the drilling threads 111, such that the dental implant can gradually cut into the gum and the alveolar bone with the help of the drilling thread 111 of each engagement section 11. By arranging the maximum outer diameter D2 of the disengagement prevention section 12 to be smaller than the minimum outer diameter D1 of each engagement section 11 between the disengagement prevention section 12 and the connection end 1a, the disengagement prevention section 12 will not affect the locking smoothness of each engagement section 11 while drilling/locking the bone implant.

After the implantation step of the dental implant, the bone tissues in the alveolar bone will gradually proceed osseointegration with the dental implant. During the osseointegration, the bone tissues will gradually envelope the outer periphery of the dental implant, and the disengagement prevention section 12 increases the contact area between the body 1 and the alveolar bone with the help of the disengagement prevention threads 121a, increasing the osseointegration effect. At the same time, during the osseointegration, not only the bone tissues growing on the disengagement prevention section 12 in the form of a neck provides a resistance to prevent disengagement of the dental implant, the disengagement prevention thread 121a having a thread direction opposite to the thread direction of the drilling threads 111 can further provide a resistance opposite to the disengagement direction of the dental implant. Thus, the dental implant can be reliably positioned in the preset location without any movement. Loosening of the dental implant in the bone tissues is less likely to occur. Thus, the osseointegration rate can be effectively increased.

Figure 4:
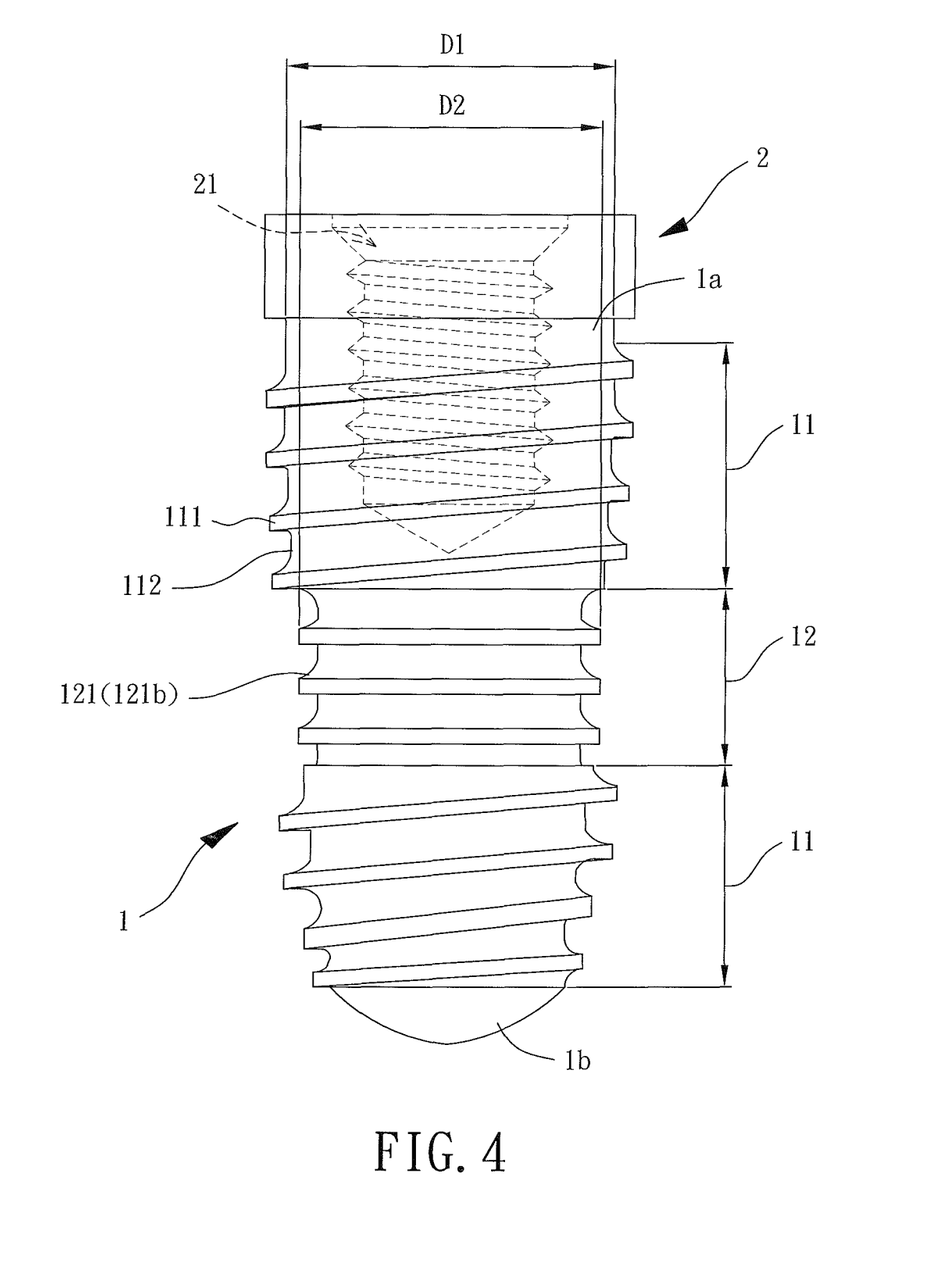
FIG. 4 is a third diagrammatic view of the structure of the first embodiment according to the present invention.

With reference to FIG. 4, in addition to the above disengagement prevention thread 121a, the coupling section 121 can be at least one protruding ring 121b disposed on the outer periphery of the body 1. Similarly, the disengagement prevention section 12 of the body 1 can be in the form of a neck, such that the maximum outer diameter D2 of the disengagement prevention section 12 can be smaller than the minimum outer diameter D1 of the engagement section 11 between the disengagement prevention section 12 and the connection end 1a. Thus, each disengagement prevention section 12 can provide a resistance opposite to the disengagement direction of the dental implant to reliably position the dental implant in the preset location without any displacement.

Furthermore, the number of the protruding rings 121b is preferably plural. In a case that the disengagement prevention section 12 includes a plurality of protruding rings 121b, the parameters, such as the spacings or the inclination angles, of the protruding rings 121b can be identical or different. Although the illustrative drawings of this embodiment show that protruding rings 121b of the same specification are disposed at regular intervals and are orthogonal to the longitudinal axis of the body 1, restrictions to this arrangement should not be done. Furthermore, a separation portion can be provided between two adjacent protruding rings 121b. The separation portion can be a blank section free of the protruding ring 121b to present a smooth or rugged surface. Alternatively, the separation portion can include a protrusion in any form. The present invention is not limited in this regard.

Furthermore, the coupling section 121 of the disengagement prevention section 12 can be free of any threads, protruding rings, or any protrusions in any forms. Instead, the coupling section 121 can be a rugged face formed by sandblasting or acid etching. The rugged face can increase the contact area between the body 1 and the bone to increase the osseointegration effect.

Figure 5:
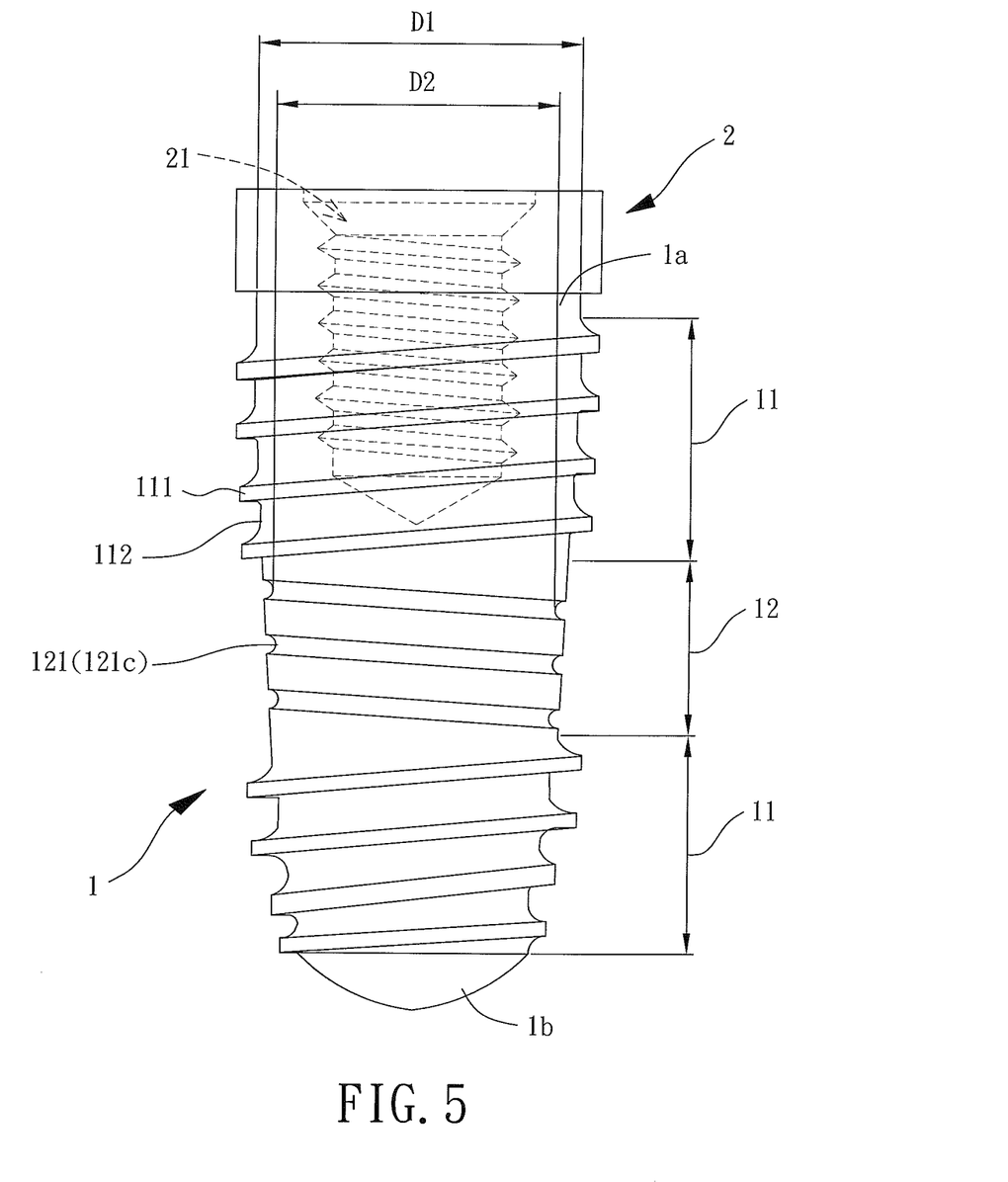
FIG. 5 is a fourth diagrammatic view of the structure of the first embodiment according to the present invention.

With reference to FIG. 5, the coupling section 121 can be at least one helical groove 121c or annular groove disposed on the outer periphery of the body 1, such that the disengagement prevention section 12 of the body 1 does not have to be in the form of a neck while still making the maximum outer diameter D2 of the disengagement prevention section 12 be smaller than the minimum outer diameter D1 of the engagement section 11 between the disengagement prevention section 12 and the connection end 1a. Thus, the contact area between the body 1 and the bone can be increased with the help of the at least one helical groove 121c or annular groove, increasing the osseointegration effect. Furthermore, the at least one helical groove 121c or annular groove further increases the resistance opposite to the disengagement direction of the dental implant to reliably position the dental implant in the preset location without any displacement.

Figure 6:
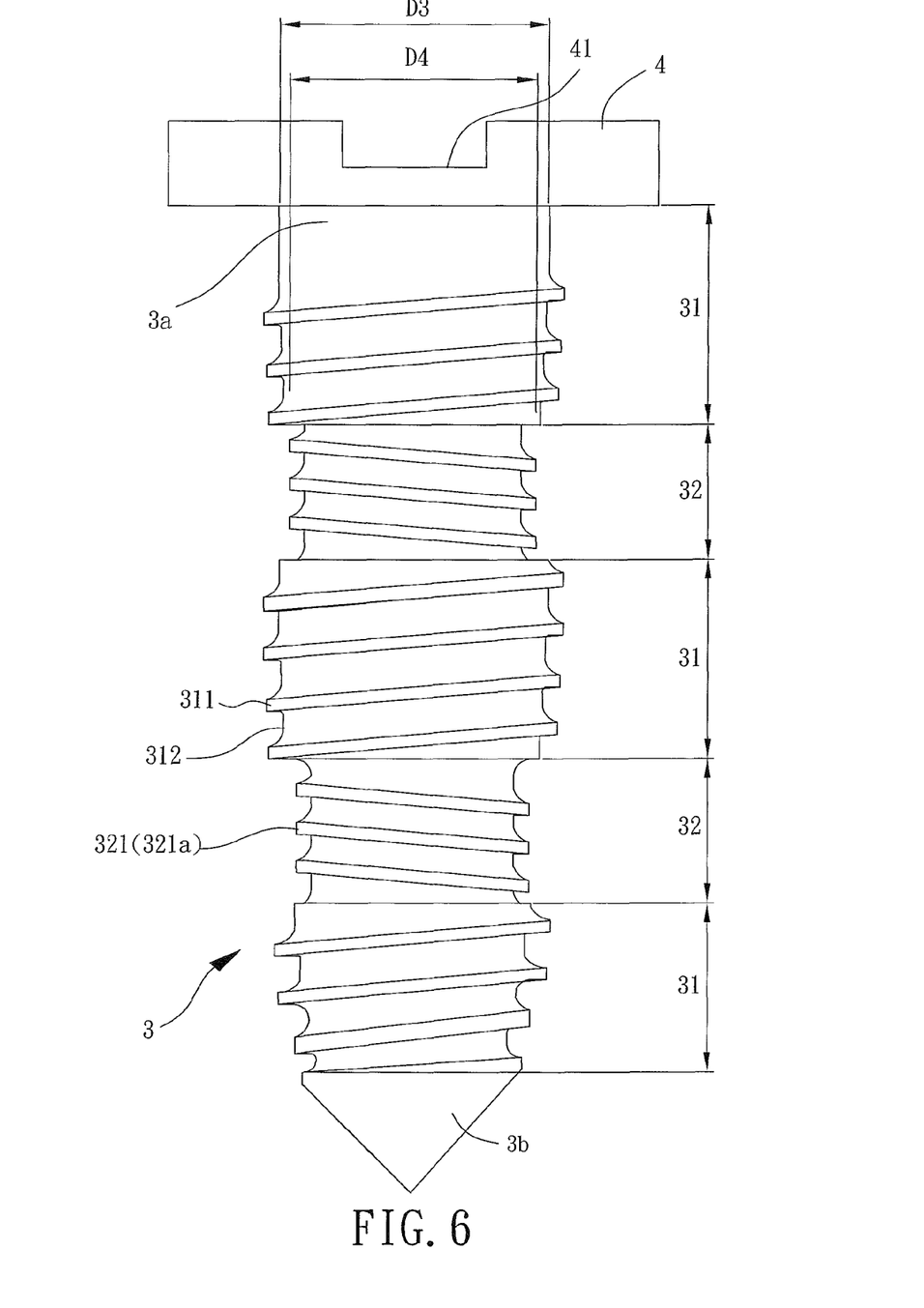
FIG. 6 is a diagrammatic view of a structure of a second embodiment according to the present invention.

With reference to FIG. 6, the bone implant of the second embodiment according to the present invention is a bone nail. The bone nail includes a body 3 and a restraining head 4. The restraining head 4 is mounted on an end of the body 3. The bone nail is used to provide a temporarily anchoring function, such as for fixing a bone plate. The bone nail can be made of a biologically absorbable material to be absorbed by a biological body after having been implanted for a period of time, eliminating the need of removal by surgery. In a case that the bone nail is used to provide a permanent anchoring function, such as for fixing an artificial joint, the bone nail can be selectively made of a biologically non-absorbable material.

The body 3 includes a connection end 3a and a drill end 3b respectively on two ends thereof. The body 3 includes a plurality of engagement sections 31 between the connection end 3a and the drill end 3b. A disengagement prevention section 32 is provided between two adjacent engagement sections 31. In an exemplified example shown in the illustrative drawings of this embodiment, the body 3 includes three engagement sections 31 and two disengagement prevention sections 32.

In this embodiment, each engagement section 31 includes a drilling thread 311 disposed on an outer periphery of the body 3. The drilling threads 311 of the engagement sections 31 have the same thread direction and preferably have the same thread angle. A groove section 312 is formed in the pitch of each drilling thread 311. The body 31 includes a minimum outer diameter D3 at the groove section 312 of each engagement section 31. The disengagement prevention section 32 includes a coupling section 321 on the outer periphery of the body 3. The body 3 includes a maximum outer diameter D4 at the disengagement prevention section 32. To avoid the smoothness from being affected while locking each engagement section 31 into a bone, the maximum outer diameter D2 should be smaller than the minimum outer diameter D3 of each engagement section 31 between the disengagement prevention section 32 and the connection end 3a.

The coupling section 321 of this embodiment can be identical to the coupling section 121 and can be at least one disengagement prevention thread 321a, protruding ring, rugged face, helical groove, or annular groove disposed on the outer periphery of the body 3. The thread directions of the disengagement prevention thread 321a and the helical groove are different from the thread direction of the drilling threads 311. Other associated structures can refer to the description in connection with the first embodiment and is, therefore, not described in details. In a case that the coupling section 321 is the disengagement prevention thread 321a, a protruding ring, or a rugged face, the disengagement prevention section 32 of the body 3 can be in the form of a neck. In another case that the coupling section 321 is a helical groove or an annular groove, the disengagement prevention section 32 of the body 3 does not have to be in the form of a neck. In either case, the maximum outer diameter D2 of the disengagement prevention section 32 can be smaller than the minimum outer diameter D3 of each engagement section 31 between the disengagement prevention section 32 and the connection end 3a. Thus, when each engagement section 31 of the body 3 of the bone nail is drilling and locking into the bone, the disengagement prevention section 32 will not affect the smoothness of the locking.

The restraining head 4 can be integrally connected to the connection end 3a of the body 3. The restraining head 4 includes a tool abutting portion 41 for abutting and positioning a tool (not shown). The tool can drive the restraining head 4 to rotate in the thread direction of drilling threads 311 to lock the body 3 into the bone. However, the structure of the restraining head 4 can be modified in response to the objects to be fixed (such as bone plates) of different forms, which can be appreciated by a person having ordinary skill in the art and which is not the features of the invention and is, therefore, not redundantly described hereinafter, nor should it be restricted to the illustrated forms.

Figure 7:
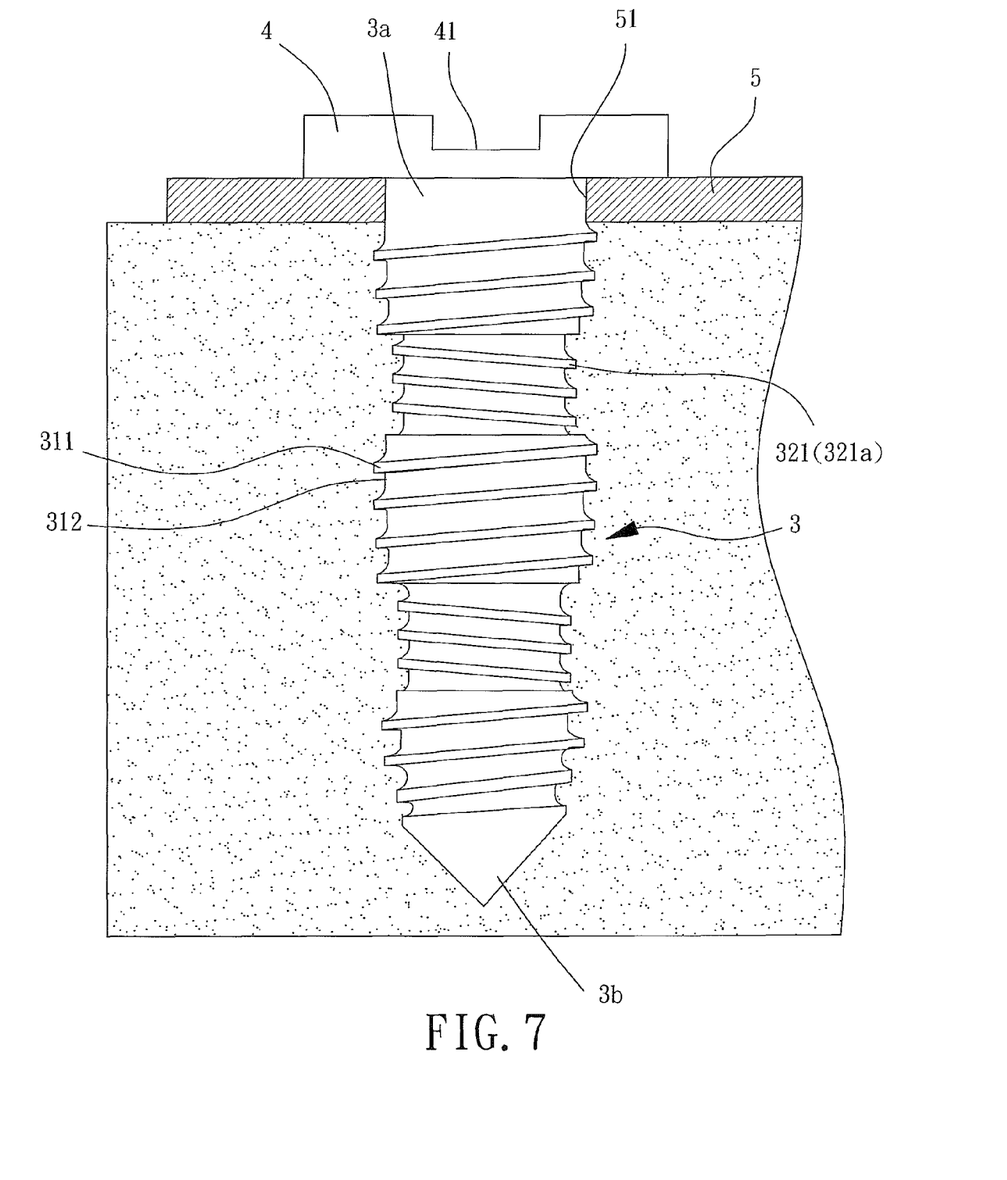
FIG. 7 is a diagrammatic view illustrating practice of the second embodiment according to the present invention.

With reference to FIG. 7, in an example of using the bone nail to fix a bone plate 5 to a surface of a bone, the body 3 extends through a drill hole 51 in the bone plate 5, and the drill end 3b of the body 3 is used as an implantation end. The body 3 is rotated by the tool, such that the bone nail can gradually cut into the bone with the help of the drilling thread 311 of each engagement section 31. Finally, the restraining head 4 abuts the surface of the bone plate 5 to avoid further penetration into the bone to thereby limit the engagement depth between the bone nail and the bone. By arranging the maximum outer diameter D4 of the disengagement prevention section 32 to be smaller than the minimum outer diameter D3 of each engagement section 31 between the disengagement prevention section 32 and the connection end 3a, the disengagement prevention section 32 will not affect the locking smoothness of each engagement section 31 during drilling/locking process.

After the implantation step of the bone nail, the bone tissues in the bone will gradually proceed osseointegration with the bone nail. During the osseointegration, the bone tissues will gradually envelope the outer periphery of the bone nail, and each disengagement prevention section 32 increases the contact area between the body 3 and the bone with the help of the coupling sections 321, increasing the osseointegration effect. At the same time, during the osseointegration, the bone tissues growing on the disengagement prevention section 32 not only breaks the torque in the thread direction of the drilling threads 311 but provides a resistance opposite to the disengagement direction of the bone nail. Thus, the bone nail can be reliably positioned in the preset location without any movement. Loosening of the bone nail in the bone tissues is less likely to occur. Thus, the osseointegration rate can be effectively increased.

In view of the foregoing, the bone implant of the present invention can use the disengagement prevention section between two adjacent engagement sections to increase the osseointegration effect and can provide a resistance opposite to the disengagement direction of the bone implant to effectively avoid loosening of the bone implant in the bone, such that the bone implant can be reliably engage in the bone without the risks of disengagement due to sliding in the reverse direction, increasing the therapy effect and efficiency to be achieved.

The foregoing merely describes the preferred embodiments of the invention and should not be construed to limit the embodying scope of the invention. Thus, simple equivalent changes and modifications based on the claims and the specification of the invention are still within the scope covered by the claims of the invention.

What is claimed is:

1. A bone implant comprising:
    a body including a connection end and a drill end respectively on two ends thereof, with the body including a plurality of engagement sections between the connection end and the drill end, with a disengagement prevention section provided between two adjacent engagement sections, with each of the plurality of engagement sections including drilling threads disposed on an outer periphery of the body, with the drilling threads of the plurality of engagement sections having a same thread direction, with the disengagement prevention section including a coupling section on the outer periphery of the body, with the disengagement prevention section having a maximum outer diameter smaller than a minimum outer diameter of each of the plurality of engagement sections between the disengagement prevention section and the connection end, and wherein the coupling section is at least one disengagement prevention thread disposed on the outer periphery of the body, and the disengagement prevention thread has a thread direction different from the thread direction of the drilling threads; and
    an abutment seat mounted on the connection end of the body, with the abutment seat including a keying recess.

2. The bone implant as claimed in claim 1, wherein a number of the disengagement prevention thread is plural.

3. The bone implant as claimed in claim 2, wherein a separation portion is provided between two adjacent disengagement prevention threads, and the separation portion is a blank section free of threads or having a protrusion.

4. The bone implant as claimed in claim 1, wherein the coupling section is at least one protruding ring disposed on the outer periphery of the body.

5. The bone implant as claimed in claim 4, wherein a number of the protruding ring is plural.

6. The bone implant as claimed in claim 5, wherein a separation portion is provided between two adjacent disengagement prevention threads, and the separation portion is a blank section free of threads or having a protrusion.

7. The bone implant as claimed in claim 1, wherein the coupling section is a rugged face.

8. The bone implant as claimed in claim 1, wherein the coupling section is at least one helical groove or annular groove disposed on the outer periphery of the body.

9. The bone implant as claimed in claim 1, wherein the plurality of drilling threads has an identical thread angle.

10. A bone implant comprising:
    a body including a connection end and a drill end respectively on two ends thereof, with the body including a plurality of engagement sections between the connection end and the drill end, with a disengagement prevention section provided between two adjacent engagement sections, with each of the plurality of engagement sections including drilling threads disposed on an outer periphery of the body, with the drilling threads of the plurality of engagement sections having a same thread direction, with the disengagement prevention section including a coupling section on the outer periphery of the body, with the disengagement prevention section having a maximum outer diameter smaller than a minimum outer diameter of each of the plurality of engagement sections between the disengagement prevention section and the connection end, and wherein the coupling section is at least one disengagement prevention thread disposed on the outer periphery of the body, and the disengagement prevention thread has a thread direction different from the thread direction of the drilling threads; and
    a restraining head mounted on the connection end of the body and having a tool abutting portion.

11. The bone implant as claimed in claim 10, wherein a number of the disengagement prevention thread is plural.

12. The bone implant as claimed in claim 11, wherein a separation portion is provided between two adjacent disengagement prevention threads, and the separation portion is a blank section free of threads or having a protrusion.

13. The bone implant as claimed in claim 10, wherein the coupling section is at least one protruding ring disposed on the outer periphery of the body.

14. The bone implant as claimed in claim 13, wherein a number of the protruding ring is plural.

15. The bone implant as claimed in claim 14, wherein a separation portion is provided between two adjacent disengagement prevention threads, and the separation portion is a blank section free of threads or having a protrusion.

16. The bone implant as claimed in claim 10, wherein the coupling section is a rugged face.

17. The bone implant as claimed in claim 10, wherein the coupling section is at least one helical groove or annular groove disposed on the outer periphery of the body.

18. The bone implant as claimed in claim 10, wherein the plurality of drilling threads has an identical thread angle.

\* \* \* \* \*